(12) United States Patent
Scarlett et al.

(10) Patent No.: US 8,600,778 B1
(45) Date of Patent: Dec. 3, 2013

(54) SITUATIONAL AWARENESS/TRIAGE TOOL FOR USE IN A CHEMICAL, BIOLOGICAL, RADIOLOGICAL NUCLEAR EXPLOSIVE (CBRNE) ENVIRONMENT

(75) Inventors: John N. Scarlett, Navaree, FL (US); Heather L. Gallup, Hanscom AFB, MA (US); David A. Smith, Dayton, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 703 days.

(21) Appl. No.: 12/551,759

(22) Filed: Sep. 1, 2009

Related U.S. Application Data

(60) Provisional application No. 61/191,530, filed on Sep. 5, 2008.

(51) Int. Cl.
*G06Q 50/00* (2012.01)

(52) U.S. Cl.
USPC .................................................. 705/3; 705/2

(58) Field of Classification Search
USPC ....................................................... 705/2–4
See application file for complete search history.

(56) References Cited

U.S. PATENT DOCUMENTS

| | | | | |
|---|---|---|---|---|
| 7,024,370 | B2 * | 4/2006 | Epler et al. | 705/3 |
| 7,761,463 | B2 * | 7/2010 | Wheeler | 707/769 |
| 2004/0073459 | A1 * | 4/2004 | Barthell | 705/2 |
| 2005/0131740 | A1 * | 6/2005 | Massenzio et al. | 705/2 |
| 2006/0218010 | A1 * | 9/2006 | Michon et al. | 705/3 |
| 2006/0224415 | A1 * | 10/2006 | Hudson et al. | 705/2 |
| 2006/0224797 | A1 * | 10/2006 | Parish et al. | 710/62 |
| 2007/0226184 | A1 * | 9/2007 | Diraimondo et al. | 707/3 |
| 2007/0288208 | A1 * | 12/2007 | Grigsby et al. | 703/2 |
| 2008/0052142 | A1 * | 2/2008 | Bailey et al. | 705/8 |
| 2008/0126417 | A1 * | 5/2008 | Mazurik | 707/104.1 |
| 2008/0177571 | A1 * | 7/2008 | Rooney et al. | 705/2 |
| 2009/0164236 | A1 * | 6/2009 | Gounares et al. | 705/2 |

OTHER PUBLICATIONS

AORN guidance statement: Mass casualty, triage, and evacuation. (2007). Association of Operating Room Nurses.AORN Journal, 85(4), 792, 794-5,797-800. doi:http://dx.doi.org/10.1016/S0001-2092(07)60154-9.*

* cited by examiner

*Primary Examiner* — Mark Holcomb
(74) *Attorney, Agent, or Firm* — AFMCLO/JAZ; Chastity Whitaker

(57) ABSTRACT

A method of managing patient care and emergency response following a Chemical, Biological, Radiological, or Nuclear Explosive (CBRNE) attack and maintaining compliance with the Health Insurance Portability and Accountability Act (HIPAA). The method including identifying each patient with a unique patient identifier, the identifier based upon the geospatial location of the patient, the geospatial location including at least the latitude and longitude of the patient when first treated, the unique patient identifier being part of patient data. Providing a collection point of patient data to form a patient data database where in the patient location data may be used to map the location, and severity of patient injuries. The method may include using the patient database is used to assist determining the type of attack and/or assist directing the distribution of medical resources. The patient data may be updated as treatment is administered. The treatment may include medication, decontamination, vaccination or a combination thereof. The patient data may be maintained on a hardware data card with the patient. The hardware data card patient data may be integrated with HIPPA patient data at a medical facility.

10 Claims, 1 Drawing Sheet

| Temp ID<br>-83.608296.39<br>39.213013.09-3 | Blood Type<br>O+ | Age<br>25 |
|---|---|---|

| AIRWAY | BREATHING | CIRCULATION | DISABILITY | ROUTINE | HOME |

BREATHING ASSESSMENT

| RESPIRATION RATE & DEPTH | RATE<br>(BREATHS PER MIN) | S Shallow    N Normal    D Deep |
|---|---|---|
| CHEST EXPANSION | NOTES | H Hindered    N Normal    A Asymmetrical |
| BREATH SOUNDS | NOTES | D Diminished    N Normal    F/A Fluid/Air<br>C Crackle    R R    W Wheezing |
| SUBCUTANEOUS AIR | NECK PRESENT | CHEST PRESENT    PRECAUTIONS |
| PAIN WHILE BREATHING | PRESENT | FLAIL CHEST    PNEUMO    HEMO<br>SCI    HEAD TRAUMA    PENETRATE |

SITUATIONAL AWARENESS/TRIAGE TOOL FOR USE IN A CHEMICAL, BIOLOGICAL, RADIOLOGICAL NUCLEAR EXPLOSIVE (CBRNE) ENVIRONMENT

PRIORITY

This application claims priority from the USPTO provisional patent application entitled "Situational Awareness/Triage tool for use in Chemical Biological, Radiological, Nuclear Explosive (CBRNE) Environment" filed on Sep. 5, 2008, Ser. No. 61/191,530 which is hereby incorporated herein by reference.

RIGHTS OF THE GOVERNMENT

The invention described herein may be manufactured and used by or for the Government of the United States for all governmental purposes without the payment of any royalty.

BACKGROUND OF THE INVENTION

The Situational Awareness/Triage Tool for Use in a Chemical, Biological, Radiological, Nuclear, Explosive (CBRNE) Environment tool and method relates to a first-responder portable computer used to collect vital patient information such as medical/exposure history, patient identification, treatment, and environmental conditions, to ensure continuity of medical history from incident scene to permanent medical treatment facility (MTF) and provide on-scene commanders with near real-time situational awareness information which will enhance the effective and efficient use of limited resources in a CBRNE environment. The item provides several features and enhancements beyond the capabilities of current digitally formatted, medical triage tools. Furthermore, the item provides integrated situational awareness of a CBRNE environment not currently available.

Current medical triage tools and methods formatted for personal digital assistant (PDA) tools have been widely used in peacetime, non-emergency situations with success. The current tools allow for digital data storage, data retrieval, and transmission within medical facilities. Current tools are not developed for emergency, war-time applications. Additionally, the current tools do not allow for patient data retrieval and transmission in non-Health Insurance Portability and Accountability Act (HIPAA, Public Law 104-191) environments, which are common in emergency and war-time situations.

The present invention provides a tool, software, and method for providing an integrated medical information system designed to improve emergency situational awareness and medical support reach back.

SUMMARY OF THE INVENTION

The present invention includes a method of managing patient care and emergency response following a Chemical, Biological, Radiological, or Nuclear Explosive (CBRNE) attack and maintaining compliance with the Health Insurance Portability and Accountability Act (HIPAA). The method includes identifying each patient with a unique patient identifier, the identifier being based upon the geospatial location of the patient, the geospatial location including at least the latitude and longitude of the patient when first treated, the unique patient identifier being part of patient data; and providing a collection point of patient data to form a patient data database wherein the patient location data may be used to map the location and severity of patient injuries. The method may include using the patient database to assist determining the type of attack and/or assist directing the distribution of medical resources. The patient data may be updated as treatment is administered.

The treatment may include medication, decontamination, vaccination, or a combination thereof. The patient data may be maintained on a hardware data card with the patient. The hardware data card patient data may be integrated with HIPAA patient data at a medical facility.

DETAILED DESCRIPTION

The Situational Awareness/Triage Tool and Method for Use in a Chemical, Biological, Radiological, Nuclear, Explosive (CBRNE) Environment allows HIPAA compliant data sharing of specific, personal data. Protection of patient data is critical and required. The triage tool allows patient specific data to be easily removed, in near real-time, prior to data transfer, thereby assuring compliance with HIPAA.

The tool or computer based device stamps each data entry geospatially and assigns a unique patient identifier not associated with the patient's personal identification. This feature allows each patient to be tracked without the use of names, social security numbers or any other personally identifying information. Responders can then monitor victim effects and locations, patient retrieval, recovery, and evacuation in an open Emergency Operations Center forum. The geospatial information is provided by a global positioning system (GPS) within the tool, which provides the latitude and longitude of the data entry. This information may help to both uniquely identify each patient and provide a database to track injuries to specific individuals. This information may also be compiled and used to track the timeliness of patient treatment and the location of those injured.

The tool or computer based device in one embodiment is integrated with the devices of other emergency responders or emergency response teams. The devices may communicate with each other or provide data to a central database. The communication may be by WIFI, cell phone service providers, or any other means known in the art. The database may be internet or intranet based. In one embodiment, the data collected has limited access by any security means known in the art.

Patient location at injury treatment may be determined by any means known in the art. One example is extracting the Global Positioning System (GPS) geolocation coordinates from the GPS receiver included in the GPS unit. GPS receivers may transmit data using several data standards including, but not limited to, NMEA (National Maritime Electronics Association), and commercial proprietary standards. A text parser may be used to extract geolocation and time information from the GPS data stream to also provide time of treatment information.

The geolocation identification provides a means for patient care providers at the scene to collect data in compliance with the Health Insurance Portability and Accountability Act (HIPAA). Individual patient data is required to be protected by HIPAA and would need to be protected during transmission by encryption and need-to-know procedures. However, aggregate information may be useful for non-medical personnel in a command and control function for determining optimum allocation of scarce rescue and recovery resources during a crisis. To make it easier to separate and aggregate non-identifying patient information, the patient data records in one embodiment may be encoded using Extensible Markup Language (XML) using a standard set of data tags. Prior to sending patient information to a non-HIPAA protected channel, patient information that is identifying (such as service number, social security number, sponsor number, name, and/or address) may be removed from the record using an automated text processing routine.

The location and injury information may not only help focus medical support where it is needed but in a chemical or biological attack when the exact weapon is not yet known, the injury profile may also help to identify the type of weapon early. For example, an injury distribution downwind may indicate a chemical attack, while an injury distribution along travel routes may indicate a biological attack. A more circular pattern may indicate a radiological attack. Further information can be gathered by the types of injuries and the types of victims. All of this information may be used to guide a course of action in the critical first hour of attack, which can have a significant impact on the number of injuries treated as well as prevented.

The tool may also include a camera or video option. A picture of the injury may help rapidly prioritize those for treatment and provide further immediate information for identifying the type of attack that has occurred.

The Situational Awareness/Triage Tool and Method for Use in a Chemical, Biological, Radiological, Nuclear, Explosive Environment offers enhanced situational awareness to the user that is not currently available on medical triage tools. The item offers a user-friendly, touch screen application (using the finger and/or stylus), with application buttons significantly larger than typical PDA tools. This is a significant ergonomic and visual enhancement. Tools currently in use are not designed for response personnel who have donned appropriate personnel protective equipment such as full-face respirators, air supply, double layered gloves, and protective overgarments. The loss of dexterity while dressed in personal protective equipment is a limiting factor when using currently available triage tools.

The item utilizes a cross-platformed, open standards architecture using an Extensible Markup language (XML) schema which is compatible with Linux®, Mac®, and Windows® based operating systems. This is a unique feature of this item. The current PDAs in use for medical triage rely, primarily, on proprietary, non-open source systems. Furthermore, the Situational Awareness/Triage Tool for Use in a Chemical, Biological, Radiological, Nuclear Explosive Environment is based on editable text files rather than an operating system which relies on source code compilation. Changes can be made to the source code through simple changes to the easily accessible text files. The item is compatible with emerging military command and control standards.

The XML schema provides a non-proprietary language for machine to machine communication of the critical data needed in a CBRNE event. XML was selected as it is a computer language that any computer using standard software can read and display. This enables networking and easy expansion of the system. The XML schemas are easily modified to add data fields, modify data field formats, or remove unnecessary fields based on user feedback, i.e. it is possible to accomplish in near real-time. Additionally, using XML ensures the system is compatible for communicating with Cursor on Target (COT) systems, which is important for future expansion of the program to communicate with fixed/rotary wing platforms in a military environment.

Ideas for the data fields captured within the XML schema were developed after a thorough review of military and civilian triage cards, inpatient medical record forms from military MTF, and the Battlefield Medical Information System Telemedicine (BMIST) system. Functional categories were created and the data apportioned to each category, as appropriate. The XML schema was developed for each category using Microsoft Access.

Data categories that may be available in the Situational Awareness/Triage Tool for Use in a Chemical, Biological, Radiological, Nuclear, Explosive Environment include Patient (Personal) Data, Medical Status, Treatment, Provider, Transportation, and Environmental Data.

The patient tracking system also allows the tracking of multiple patients from their first triage through the hospital or final treatment. This would include initial assessments and/or drug treatments administered in a catastrophic event environment with hundreds or thousands of people needing care.

The (CBRNE) tools may include wireless enablement which can transmit or receive patient data or treatment information via data link with a Medical Center.

In one embodiment, an encrypted data card such as a SD card would stay with a patient and can be accessed by any authorized treatment official with appropriate software or (CBRNE) tool. Alternatively the unique patient identifier may be printed as a unique barcode, radio frequency identification (RFID), or other identifier, each linked to the data collected and the unique patient identifier in the patient data database.

The tool may include data entry screens including: emergency data, airway, breathing, circulation, disability, and routine information, and home.

Examples of basic information may include a description of any allergies, existing medical alerts, medications, or other medical information of interest. The medication information may include medications previously or regularly taken by the patient and those administered by the medic.

Examples of the airway assessment may include the identification of spinal injuries, secretions, vomit, blood, aspiration, or other airway issue.

Examples of the circulation information may include pulse, skin color, temperature, vital signs, or any bleeding.

Examples of the breathing assessment screen are shown in FIG. 1 for patient -83.608296,39.213013,09-3 where -83.608296,39.213013,09 is the GPS location and -3 is the third patient at that location. FIG. 1 illustrates one embodiment for an on-screen breathing assessment. The screen may include the temporary patient identification and a listing of available tabs for different screens. As shown in FIG. 1, these screens include airway, breathing, circulation, disability, routine, and home. Specific data may include respiration rate, respiration depth, chest expansion, breath sounds, subcutaneous air, and pain while breathing. This data may be entered by touch screen and/or voice recognition or any other means known in the art.

The tool may further include voice activation generation, which would allow the system to respond to the operator's verbal commands.

The tool preferably may be integrated with compact medical devices. While in one embodiment the operator may enter the patient information with a keyboard stylus, it may also be entered by wireless communication with Bluetooth® blood pressure measuring devices to heart monitors, oxygen readers, or even hand-held computer tomography scanners. Any portable medical device may be integrated into the tool for data entry. In one embodiment, portable gas detectors, radiation detectors, chemical detectors, or spectrometers may also be in communication with a tool to provide both data and warning of potential dangers.

A collection point for the data or a patent data database may be used to provide an integrated injury picture to improve combat and emergency care by targeting the right staff and equipment to the point of most urgent need. In one embodiment, the patient data database may be maintained over time so a history of the patients' vital statistics such as heart rate, blood pressure, etc. may be maintained and reviewed as necessary by medical professionals.

What is claimed is:

1. A method of managing patient care and emergency response following a Chemical, Biological Radiological, or Nuclear Explosive (CBRNE) attack and maintaining compliance with laws and regulations concerning healthcare data storage and transmission requirements, the method comprising:

locating a plurality of patients at the CBRNE attack;

administering a treatment to each of the plurality of patients at a patient location for an injury resulting from the CBRNE attack; and utilizing a computer processor to perform the following steps:

recording at least one personally identifying patient information and the administered treatment as patient data for each of the plurality of patients, transforming and transmitting the patient data in a process compliant with laws and regulations concerning healthcare data storage and transmission requirements, the process comprising:

determining a geospatial location for each of the plurality of patients, the geospatial location including a latitude and a longitude corresponding to the respective patient location;

generating a unique patient identifier for each of the plurality of patients, the unique patient identifier based on the geospatial location of each of a respective one of the plurality of patients;

associating the unique patient identifier with the respective patient data; and transmitting the patient data for at least one of the plurality of patients to a collection point to form a patient database, wherein transmitting the patient data further comprises:

encrypting the patient data that is transmitted to a collection point compliant with laws and regulations concerning healthcare data storage and transmission requirements, and removing the at least one personally identifying patient information from the patient data that is transmitted to a collection point that is not compliant with laws and regulations concerning healthcare data storage and transmission requirements; and determining a type of attack from patient data in the patient database, the type of attack being at least one of chemical, biological, radiological or nuclear explosive.

2. The method of claim 1 wherein the patient database is used to assist in directing distribution of medical resources.

3. The method of claim 1 wherein the patient data is updated as treatment is administered.

4. The method of claim 3 wherein the treatment includes medication, decontamination, vaccination or a combination thereof.

5. The method of claim 1 wherein the patient data is maintained on a hardware data card with the patient.

6. The method of claim 5 wherein the hardware data card patient data is integrated with patient data at a medical facility.

7. The method of claim 1 further comprising monitoring environmental conditions using at least one portable monitoring device, wherein the portable monitoring device is integrated with the portable computer-based tool, the portable monitoring device comprising at least one of a gas detector, a radiation detector, a chemical detector, and a spectrometer.

8. The method of claim 1 further comprising wirelessly transmitting the patient data to the collection point.

9. The method of claim 8 wherein the patient data further comprises a photograph or video, the photograph or video comprising a visual depiction of an injury to the patient.

10. The method of claim 1 further comprising mapping at least one of injury severity and injury distribution based on the patient data in the patient database.

\* \* \* \* \*